United States Patent [19]

Müller et al.

[11] Patent Number: 5,576,342
[45] Date of Patent: Nov. 19, 1996

[54] PHENYLGLYCINAMIDES OF HETEROCYCLICALLY SUBSTITUED PHENYLACETIC ACID DERIVATIVES

[75] Inventors: Ulrich Müller, Wuppertal; Jürgen Dressel, Radevormwald; Peter Fey, Wuppertal; Rudolf Hanko, Essen; Walter Hübsch; Thomas Krämer, both of Wuppertal; Matthias Müller-Gliemann, Solingen; Martin Beuck, Erkrath; Stanislav Kazda, Wuppertal; Stefan Wohlfeil, Hilden; Andreas Knorr, Erkrath; Johannes-Peter Stasch, Solingen, all of Germany; Siegfried Zaiss, Wuppertal, all of Germany

[73] Assignee: Bayer Aktiengesellschaft, Leverkusen, Germany

[21] Appl. No.: 210,810

[22] Filed: Mar. 18, 1994

Related U.S. Application Data

[63] Continuation-in-part of Ser. No. 25,479, Mar. 3, 1993, Pat. No. 5,352,687, and Ser. No. 25,495, Mar. 3, 1993, Pat. No. 5,420,149.

[30] Foreign Application Priority Data

Mar. 26, 1993 [DE] Germany .......................... 43 09 968.8

[51] Int. Cl.⁶ ..................... A61K 31/535; A61K 31/415; C07D 413/10; C07D 403/10

[52] U.S. Cl. .................... 514/399; 514/235.8; 514/252; 514/326; 514/333; 514/341; 544/139; 544/370; 546/210; 546/256; 546/274.7; 546/275.1; 548/338.1

[58] Field of Search ................. 514/235.8, 252, 514/326, 333, 341, 399; 544/139, 370; 546/210, 256, 278; 548/338.1

[56] References Cited

U.S. PATENT DOCUMENTS

| | | | |
|---|---|---|---|
| 5,128,355 | 7/1992 | Carini et al. | 514/381 |
| 5,352,687 | 10/1994 | Muller et al. | 514/341 |
| 5,420,149 | 5/1995 | Muller et al. | 514/399 |

OTHER PUBLICATIONS

The Journal of Cell Biology, vol. 50, 1971, pp. 172–186; "The Smooth Muscle Cell . . . ", R. Ross.

McGraw–Hill Series in Advanced Chemistry, 1962; "Stereochemistry of Carbon Compounds", E. L. Eliel, 6 pages.

Chemical Abstracts, vol. 81, 1974, p. 577, 34—Amino Acids/Peptides/Proteins; CA#169829k: "Chemistry and mechanism of new angiotensin II antagonists", H. Wissmann et al.

*Primary Examiner*—Patricia L. Morris
*Attorney, Agent, or Firm*—Sprung Horn Kramer & Woods

[57] ABSTRACT

Phenylglycinamides of heterocyclically substituted phenylacetic acid derivatives are prepared by reacting phenylacetic acids with glycinamides. The compounds can be used as active compounds in medicaments.

9 Claims, No Drawings

PHENYLGLYCINAMIDES OF HETEROCYCLICALLY SUBSTITUED PHENYLACETIC ACID DERIVATIVES

This application is a continuation-in-part of application Ser. No. 25,479, filed Mar. 3, 1993, now U.S. Pat. No. 5,352,687, and of application Ser. No. 25,495, filed Mar. 3, 1993, now U.S. Pat. No. 5,420,149.

The invention relates to phenylglycinamides of heterocyclically substituted phenylacetic acid derivatives, processes for their preparation and their use in medicaments, in particular as hypotensive and antiatherosclerotic agents.

It is known that renin, a proteolytic enzyme, eliminates the decapeptide angiotensin I from angiotensinogen in vivo, and the angiotensin I is in turn degraded in the lung, the kidneys or other tissues to give the hypertensive octapeptide angiotensin II. The various effects of angiotensin II, such as, for example, vasoconstriction, Na$^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, cardiac muscle cells and smooth muscle cells, these growing and proliferating in an increased manner in various disease states (for example hypertension, atherosclerosis and cardiac insufficiency).

Apart from inhibition of renin activity, a possible starting point for intervention in the renin-angiotensin system (RAS) is the inhibition of the activity of the angiotensin-converting enzyme (ACE) and the blockade of angiotensin II receptors.

The present invention relates to new phenylglycinamides of heterocyclically substituted phenylacetic acid derivatives of the general formula (I)

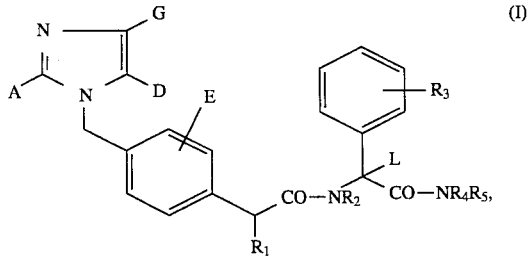

in which
A represents straight-chain or branched alkyl or alkenyl each having up to 8 carbon atoms, or represents cycloalkyl having 3 to 8 carbon atoms,
G represents hydrogen, halogen or perfluoroalkyl having up to 5 carbon atoms,
D represents a group of the formula —$CH_2$—$OR^4$ or —CO—$R^7$,
in which
$R^6$ denotes hydrogen or straight-chain or branched alkyl having up to 8 carbon atoms,
$R^7$ denotes hydrogen, hydroxyl or straight-chain or branched alkoxy having up to 8 carbon atoms,
E represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl,
L represents hydrogen or straight-chain or branched alkyl having up to 4 carbon atoms,
$R^1$ represents cycloalkyl having 3 to 8 carbon atoms, or represents straight-chain or branched alkyl having up to 8 carbon atoms, which is optionally substituted by cycloalkyl having 3 to 8 carbon atoms,
$R^2$ represents hydrogen or straight-chain or branched alkyl having up to 6 carbon atoms,
$R^3$ represents hydrogen, hydroxyl, halogen or straight-chain or branched alkoxy having up to 6 carbon atoms,
$R^4$ and $R^5$ are identical or different and represent hydrogen, phenyl, pyridyl, cycloalkyl having 3 to 8 carbon atoms, or straight-chain or branched alkyl having up to 8 carbon atoms, which is optionally substituted by hydroxyl, pyridyl, carboxyl, straight-chain or branched alkoxycarbonyl having up to 6 carbon atoms or by a group of the formula —$NR^8R^9$,
in which
$R^8$ and $R^9$ are identical or different and denote hydrogen or straight-chain or branched alkyl having up to 4 carbon atoms
or
$R^4$ and $R^5$, together with the nitrogen atom, form a 6-membered saturated heterocycle having up to 3 heteroatoms from the group consisting of S, N and O, and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the new phenylglycinamides of heterocyclically substituted phenylacetic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines such as, for example, ethylamine, di- or triethylamine, di- or tri-ethanolamine, dicyclohexylamine, dimethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the enantiomers or diastereomers or to their respective mixtures. Like the diastereomers, the racemic forms can be separated into the stereoisomerically uniform constituents in a known manner. [cf. E. L. Eliel, Stereochemistry of Carbon Compounds, McGraw Hill, 1962].

Preferred compounds of the general formula (I) are those in which
A represents straight-chain or branched alkyl or alkenyl each having up to 6 carbon atoms, or represents cyclopropyl, cyclobutyl, cyclopentyl, cyclohexyl or cycloheptyl,
G represents hydrogen, fluorine, chlorine, bromine or perfluoroalkyl having up to 4 carbon atoms,
D represents a group of the formula —$CH_2$—$OR^6$ or —CO—$R^7$,
in which
$R^6$ denotes hydrogen or straight-chain or branched alkyl having up to 6 carbon atoms, $R^7$ denotes hydrogen, hydroxyl or straight-chain or branched alkoxy having up to 6 carbon atoms, E represents hydrogen, fluorine, chlorine, bromine, trifluoromethyl, carboxyl or straight-chain or branched alkyl, alkoxy or alkoxycarbonyl each having up to 4 carbon atoms, L represents hydrogen or methyl $R^1$ represents cyclopropyl, cyclopentyl, cyclohexyl or cycloheptyl, or represents straight-chain or branched alkyl having up to 4 carbon atoms, which is optionally substituted by cyclopropyl, cyclopentyl, cyclohexyl or cycloheptyl, $R^2$ represents hydrogen or straight-chain or branched alkyl having up to 4 carbon atoms, $R^3$ represents hydrogen, hydroxyl, fluorine, chlorine, bromine or straight-chain or branched alkoxy having up to 4 carbon atoms, $R^4$ and $R^5$ are identical or different and represent hydrogen, pyridyl, cyclopentyl, cyclohexyl, phenyl or straight-chain or branched alkyl having up to 6 carbon atoms, which is optionally substituted by hydroxyl, pyridyl, carboxyl, straight-chain or branched alkoxycarbonyl having up to 4 carbon atoms or by a group of the formula —$NR^8R^9$, in which $R^8$ and $R^9$ are identical or different and denote hydrogen or methyl, or $R^4$ and $R^5$ together with the nitrogen atom, form a morpholine, piperazine or piperidine ring, and their salts.

Particularly preferred compounds of the general formula (I) are those in which

A represents straight-chain or branched alkyl or alkenyl each having up to 4 carbon atoms, or represents cyclopropyl, cyclopentyl or cyclohexyl, G represents hydrogen, fluorine, chlorine or perfluoroalkyl having up to 2 carbon atoms, D represents a group of the formula —$CH_2$—$OR^6$ or —CO—$R^7$, in which $R^6$ denotes hydrogen or straight-chain or branched alkyl having up to 4 carbon atoms, $R^7$ denotes hydrogen, hydroxyl or straight-chain or branched alkoxy having up to 4 carbon atoms, E represents hydrogen, fluorine, chlorine, bromine, trifluoromethyl, trifluoromethoxy or methyl L represents hydrogen or methyl, $R^1$ represents cyclopentyl, cyclohexyl or cycloheptyl, or represents straight-chain or branched alkyl having up to 3 carbon atoms, which is optionally substituted by cyclopentyl, cyclohexyl or cycloheptyl, $R^2$ represents hydrogen, methyl or ethyl, $R^3$ represents hydrogen, hydroxyl, fluorine, chlorine, bromine or methoxy, $R^4$ and $R^5$ are identical or different and represent hydrogen, pyridyl, cyclohexyl, phenyl or straight-chain or branched alkyl having up to 4 carbon atoms, which is optionally substituted by hydroxyl, pyridyl, carboxyl, straight-chain or branched alkoxycarbonyl having up to 3 carbon atoms, amino or dimethylamino, or $R^4$ and $R^5$, together with the nitrogen atom, form a morpholine, piperazine or piperidine ring, and their salts.

Processes for the preparation of the compounds of the general formula (I) according to the invention have additionally been found, characterized in that

[A] either compounds of the general formula (II)

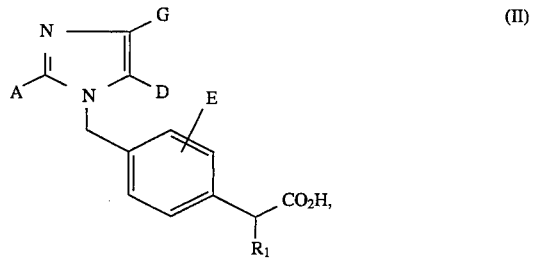

in which

A, G, D, E and $R^1$ have the abovementioned meaning, are reacted with compounds of the general formula (III)

in which

L, $R^2$, $R^3$, $R^4$ and $R^5$ have the abovementioned meaning, or

[B] compounds of the general formula (IV)

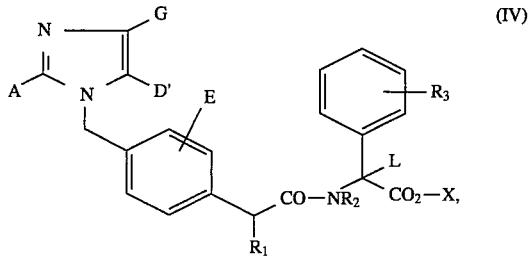

in which

L, A, B, $R^1$, $R^2$ and $R^3$ have the abovementioned meaning,

D' represents the —$CH_2$—OH— group and

X represents $C_1$–$C_4$-alkyl, are reacted with amines or ammonia of the general formula (V)

in which $R^4$ and $R^5$ have the abovementioned meaning, in inert solvents, in the presence of a base and of an auxiliary, and in the case where $R^2$, $R^4$ and/or $R^5 \ne H$, an alkylation follows, and the substituents A, G, D' and E are converted by customary methods, such as, for example reduction, and if appropriate the isomers are separated, and in the case of the preparation of the salts reacted with an appropriate base or acid.

The process according to the invention can be illustrated by way of example by the following reaction scheme:

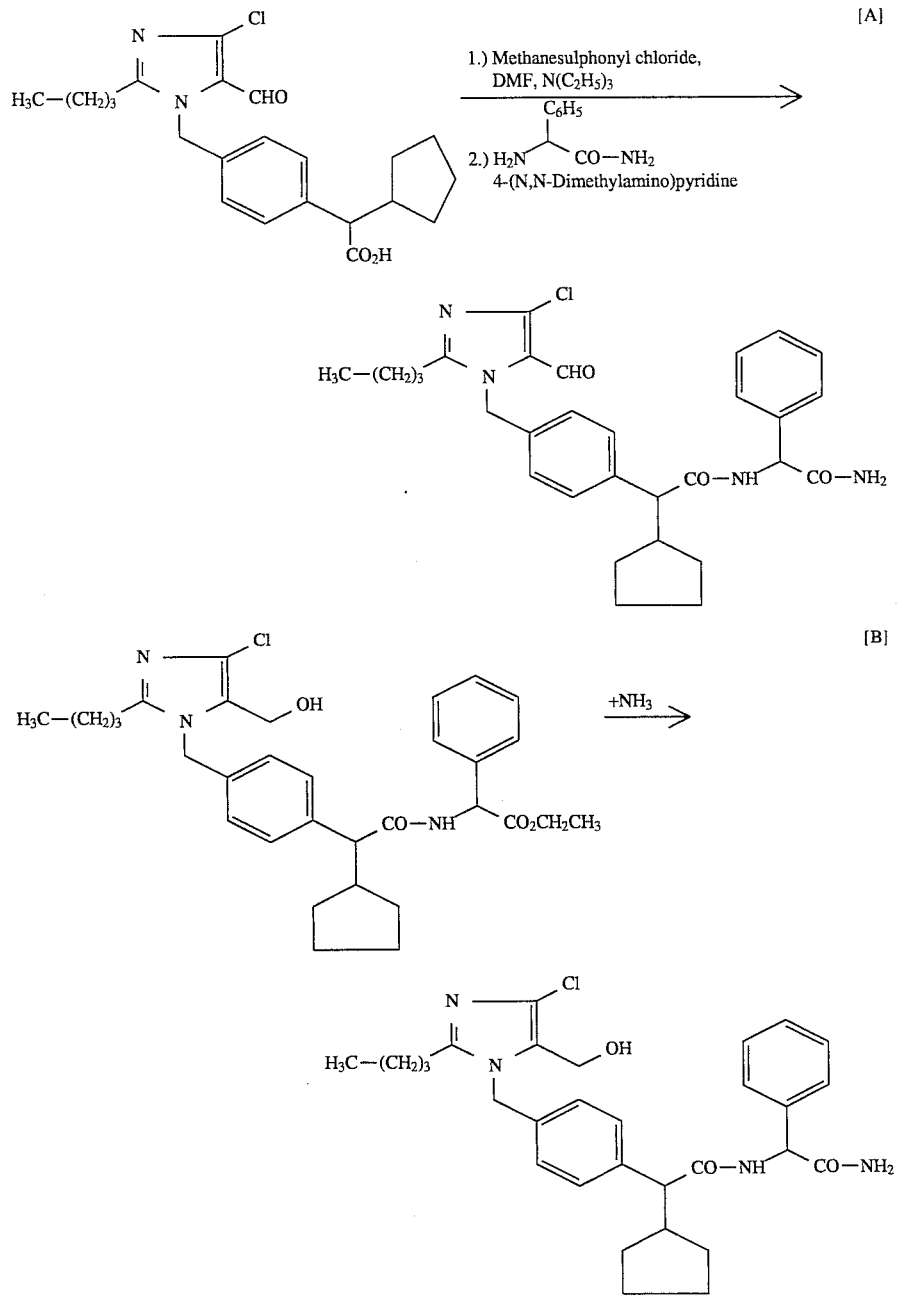

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane, or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

The bases employed for the process according to the invention can in general be inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, 4-(N,N-dimethylamino)pyridine, methylpiperidine or morpholine. It is also possible to employ alkali metals such as sodium or their hydrides such as sodium hydride as bases. Sodium hydride, potassium carbonate, triethylamine, pyridine, potassium tert-butoxide and 4-(N,N-dimethylamino)pyridine are preferred.

In general the base is employed in an amount from 0.05 to 10 mol, preferably from 1 mol to 2 mol, relative to 1 mol of the compound of the formula (III).

The process according to the invention is in general carried out in a temperature range from −30° C. to +100° C., preferably from −30° C. to +60° C.

The process according to the invention is in general carried out at normal pressure. However, it is also possible to carry out the process at elevated pressure or at reduced pressure (for example in a range from 0.5 to 5 bar).

The amidation is in general carried out in one of the abovementioned solvents, preferably in N,N-dimethylformamide.

The amidation is in general optionally carried out via the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

The amidation or acylsulphonamidation is in general carried out in a temperature range from −50° C. to +80° C., preferably from −30° C. to +20° C., and at normal pressure.

In addition to the abovementioned bases, suitable bases for this reaction are preferably triethylamine and/or dimethylaminopyridine, DBU or DABCO.

The base is employed in an amount from 0.5 mol to 10 mol, preferably from 1 mol to 5 mol, relative to 1 mol of the appropriate carboxylic acid.

Acid-binding agents which can be employed for the amidation or sulphoamidation are alkali metal or alkaline earth metal carbonates such as sodiumcarbonate or potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[4.3.0]non-5-ene (DBN) or 1,5-diazabicyclo[5.4.0]undec-5-ene (DBU). Triethylamine is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate, or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The reduction of alkoxycarbonyl compounds or aldehydes to the corresponding alcohols is in general carried out using hydrides, such as lithiumaluminium hydride or sodium borohydride, preferably using lithiumaluminium hydride in inert solvents such as ethers, hydrocarbons or alcohols or mixtures thereof, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C. preferably from +20° C. to +100° C., at normal pressure.

The alkylation is in general carried out in one of the abovementioned solvents using alkylating agents such as, for example, ($C_1$–$C_8$)-alkyl halides, sulphonic acid esters or substituted or unsubstituted ($C_1$–$C_6$)-dialkyl or ($C_1$–$C_{10}$)-diaryl sulphates, preferably methyl iodide, p-toluenesulphonic esters or dimethyl sulphate.

The compounds of the general formula (II) are new and can be prepared by reacting compounds of the general formula (VI)

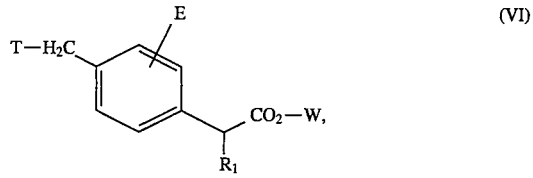

in which

E and $R^1$ have the abovementioned meaning,

T represents a typical leaving group such as, for example, chlorine, bromine, iodine, tosylate or mesylate, preferably bromine, and W represents straight-chain or branched ($C_1$–$C_4$)-alkyl, first with imidazoles of the general formula (VII)

in which

A, G and D have the abovementioned meaning, in one of the abovementioned inert solvents, if appropriate in the presence of a base, and under a protective gas atmosphere.

and in a last step hydrolysing the esters according to customary methods.

A suitable solvent for the reaction with the compounds of the general formula (IV) is preferably dimethylformamide.

The bases employed are preferably sodium hydride, potassium carbonate, triethylamine, pyridine and potassium tert-butoxide.

In general, the base is employed in an amount from 0.05 mol to 10 mol, preferably from 1 mol to 2 mol, relative to 1 mol of the compound of the formula (IV).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide.

Alcohols such as methanol, ethanol, propanol or isopropanol are particularly preferably used. It is also possible to employ mixtures of the solvents mentioned.

The hydrolysis is preferably carried out using acids such as, for example, trifluoroacetic acid, acetic acid, hydrochloric acid, hydrochloric acid/dioxane, hydrobromic acid, methanesulphonic acid, sulphuric acid or perchloric acid, particularly preferably using trifluoroacetic acid or hydrochloric acid/dioxane.

The hydrolysis is in general carried out in a temperature range from 0° C. to +100° C. preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has also proven advantageous in this case in the preparation of the carboxylic acids to acidify the basic reaction mixture from the hydrolysis in a second step without isolation of the carboxylates. The acids can then be isolated in a customary manner.

The compounds of the general formulae (III), (V) and (VII) are known.

The compounds of the general formula (VI) are for the most part new and can be prepared by reacting the corresponding 4-methyl compounds in the sense of a substitution, for example by halogenation in the presence of one of the abovementioned bases and/or auxiliaries and of one of the solvents.

The compounds of the general formula (IV) are new per se and can be prepared, for example, by reaction of the compounds of the general formula (II) with compounds of the general formula (VIII)

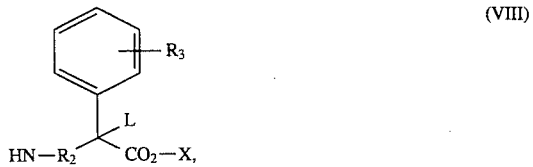

in which

L, $R^2$, $R^3$ and X have the abovementioned meaning, as described in [A].

The compounds of the general formula (VIII) are known in some cases or can be prepared by customary methods.

The compounds of the general formula (I) according to the invention exhibit an unforeseeable, useful spectrum of pharmacological action.

The compounds according to the invention have a specific A II-antagonistic action, since they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, disorders of the brain function, ischaemic cerebral diseases, peripheral circulatory disorders, functional disorders of the kidney and adrenal gland, bronchospastic diseases and respiratory tract diseases having a vascular component, sodium retention and oedemas.

Investigation of the inhibition of the contraction induced by agonists

Rabbits of either sex are stunned by a blow to the back of the head and exsanguinated, or in some cases anaesthetized with Nembutal (about 60–80 mg/kg i.v.) and sacrificed by opening the thorax. The thorax aorta is removed, freed from adhering connective tissue, divided into ring segments 1.5 mm wide and individually transferred under an initial loading of about 3.5 g to 10 ml organ baths containing Krebs-Henseleit nutrient solution, which is temperature-controlled at 37° C. and aerated with 95% $O_2$/5% $CO_2$, of the following composition: 119 mmol/l of NaCl; 2.5 mmol/l of $CaCl_2 \times 2H_2O$; 1.2 mmol/l of $KH_2PO_4$; 10 mmol/l of glucose; 4.8 mmol/l of KCl; 1.4 mmol/l of $MgSO_4 \times 7H_2O$ and 25 mmol/l of $NaHCO_3$.

The contractions are detected isometrically by Statham UC2 cells by means of bridge amplifiers (ifd Mülheim or DSM Aalen) and digitalized and assessed by means of A/D converters (System 570, Keithley Munich). Agonist dose response curves (DRC) are carried out hourly. With each DRC, 3 or 4 individual concentrations are applied to the baths at a 4 min interval. After the end of the DRC and subsequent washing-out cycles (16 times in each case about 5 sec/min with the abovementioned nutrient solution), a 28-minute rest or incubation phase follows, during which the contractions as a rule reach the starting value again.

The height of the 3rd DRC, in a normal case, is used as a reference variable for the assessment of the test substance to be investigated in further runs, which is applied to the baths in the following DRCs in increasing doses in each case at the start of the incubation period. Each aorta ring is in this case stimulated for the whole day, always with the same agonist.

| Agonists and their standard concentrations (application volume per individual dose = 100 μl): | | |
|---|---|---|
| KCl | 22.7; 32.7; 42.7; 52.7 | mmol/l |
| L-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$; | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarization or other agonists was not inhibited or only weakly inhibited at high concentrations.

Blood pressure measurements on the angiotensin II-infused rat

Male Wistar rats (Moellegaard, Copenhagen, Denmark) having a body weight of 300–350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins.

After administration of the ganglionic blocker pentolinium (5 mg/kg i.v.), the angiotensin II infusion (0.3 pg/kg/min) is started. As soon as the blood pressure values have reached a stable plateau, the test substances are either administered intravenously or orally as a suspension or solution in 0.5% Tylose. The blood pressure changes under effect of substance are given in the table as mean values±SEM.

Determination of the antihypertensive activity in conscious hypertensive rats

The oral antihypertensive activity of the compounds according to the invention was tested in conscious rats using surgically induced unilateral renal artery stenosis. To do this, the right renal artery was constricted with a silver clip of 0.18 mm internal width. In this form of hypertension, the plasma renin activity is increased in the first six weeks after intervention.

The arterial blood pressure of these animals was measured in a blood-free manner at defined time intervals after substance administration using the "tail cuff". The substances to be tested were suspended in a Tylose suspension and administered intragastrally ("orally") in various doses by stomach tube. The compounds according to the invention reduce the arterial blood pressure of the hypertensive rats at a clinically relevant dose.

Additionally, the compounds according to the invention inhibit the specific binding of radioactive angiotensin II in a concentration-dependent manner.

Interaction of the compounds according to the invention with the angiotensin II receptor in membrane fractions of the adrenal gland cortex (bovine)

Bovine adrenal gland cortices (AGC), which have been freshly removed and carefully freed from gland medulla, are comminuted in sucrose solution (0.32M) with the aid of an Ultra-Turrax (Janke & Kunkel, Staufen i.B.) to give a coarse membrane homogenate and partially purified in two centrifugation steps to give membrane fractions.

The receptor binding investigations are carried out on partially purified membrane fractions of bovine AGC using radioactive angiotensin II in an assay volume of 0.25 ml, which specifically contains the partially purified membranes (50–80 µg), $^3$H-angiotensin II (3–5 nM), test buffer solution (50 mM Tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

Investigation of the inhibition of the proliferation of smooth muscle cells by the compounds according to the invention To determine the antiproliferative action of the compounds, smooth muscle cells are used which are obtained from aortas of rats by the media explant technique [R. Ross, J. Cell. Biol. 50, 172, 1971]. The cells are inoculated in suitable culture dishes, as a rule 96-hole plates, and cultured in 5% $CO_2$ at 37° C. for 2–3 days in medium 199 containing 7.5% FCS and 7.5% NCS, 2 mM L-glutamine and 15 mM HEPES, pH 7.4. The cells are then synchronized by withdrawal of serum for 2–3 days and then stimulated into growth with serum. Test compounds are simultaneously added. After 16–20 hours, 1 µCi of thymidine is added and after a further 4 hours the incorporation of this substance into the TCA-precipitatable DNA of the cells is determined. To determine the $IC_{50}$ values, the active compound concentration is calculated which, on sequential dilution of the active compound, causes semi-maximal inhibition of the thymidine incorporation produced by 10% FCS.

TABLE B

| Ex. No. | $IC_{50}$ [nM] |
|---------|----------------|
| 1       | 1.0            |
| 6       | 0.2            |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound using suitable liquid excipients can be employed.

In general, it has proven advantageous in the case of intravenous administration to administer amounts of about 0.001 to 1 mg/kg, preferably about 0.01 to 0.5 mg/kg of body weight to achieve effective results, and in the case of oral administration the dose is about 0.01 to 20 mg/kg, preferably 0.1 to 10 mg/kg of body weight.

In spite of this, it may sometimes be necessary to depart from the amounts mentioned, in particular depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

Eluents (A) Petroleum ether:ethyl acetate=3:7
(B) Dichloromethane:methanol=8:1
(C) Petroleum ether:ethyl acetate=1:4
(D) Petroleum ether:ethyl acetate=1:1
(E) Dichloromethane:methanol=5:1
(F) Dichloromethane:ethyl acetate=10:1
(G) Dichloromethane:methanol=10:1
(H) Petroleum ether:ethyl acetate=2:1
(I) Dichloromethane:methanol=20:1

STARTING COMPOUNDS

Example I tert-Butyl 4-methylphenylacetate

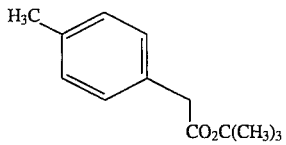

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2N hydrochloric acid and water. The organic phase is concentrated and distilled. Yield: 408 g (66% of theory) Boiling point: 73°–78° C./0.2 mm

Example II tert-Butyl 2-cyclopentyl-2-(4-methylphenyl)acetate

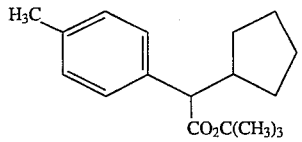

33.5 g (0.3 mol) of potassium tert-butoxide are initially introduced at 0° C. into 100 ml of DMF with exclusion of moisture and 51.6 g (0.25 mol) of tert-butyl 4-methylphenylacetate in 250 ml of DMF are added dropwise. The mixture is stirred at 0° C. for 30 min and 32.2 ml (0.3 mol) of cyclopentyl bromide in 150 ml of DMF are added dropwise at 5°–15° C. and the mixture is stirred at 25° C. for 20 h. After concentration, the residue is partitioned between water/diethyl ether, and the ether phase is dried over sodium sulphate and concentrated. The product crystallizes out. Yield: 67 g (97.5% of theory) Melting point: 51°–53° C.

Example III tert-Butyl 2-(4-bromomethyl-phenyl)-2-cyclopentyl-acetate

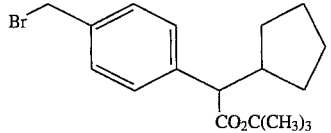

27.4 g (0.1 mol) of tert-butyl 2-cyclopentyl-2-(4-methylphenyl)-acetate are dissolved in 200 ml of carbon tetrachloride and heated to boiling. After addition of 0.82 g of azobisisobutyronitrile, 18.7 g (0.105 mol) of N-bromosuccinimide are added in portions and the mixture is then refluxed for 1 h, cooled to 0° C. and succinimide is filtered off. After concentration of the filtrate the product precipitates. It is washed with petroleum ether (40/60) and dried. Yield: 20 g (57% of theory) Melting point: 73°–76° C.

Example IV tert-Butyl 2-[4-(2-butyl-4-chloro-5-formyl-imidazol-1-ylmethyl)phenyl]-2-cyclopentyl-acetate

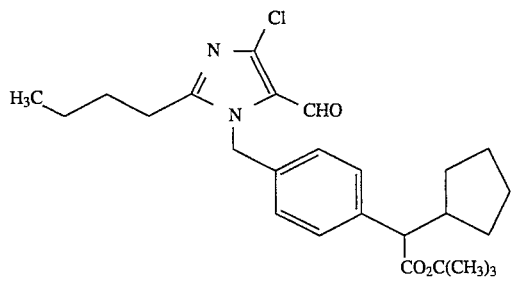

1.6 g (0.053 mol) of sodium hydride (80% strength) are suspended in 50 ml of DMF under protective gas, 10 g (0.053 mol) of 2-butyl-5-formyl-4-chloroimidazole (preparation according to EP 324,377) in 100 ml of DMF are added dropwise at 0° C. then the mixture is stirred at 0° C. for 15 min and 18.9 g (0.053 mol) of tert-butyl 2-(4-bromomethylphenyl)-2-cyclopentylacetate in 100 ml of DMF are added dropwise. The mixture is additionally stirred at 0° C. for 2 h, the solvent is evaporated off, the residue is taken up in diethyl ether, the solid is filtered off and after concentration the residue is chromatographed on silica gel 60 using dichloromethane. Yield: 16.2 g (66.7% of theory) Melting point: 101°–102° C.

Example V

2-[4-(2-Butyl-4-chloro-5-formyl-imidazol-1-yl-methyl)phenyl]-2-cyclopentylacetic acid

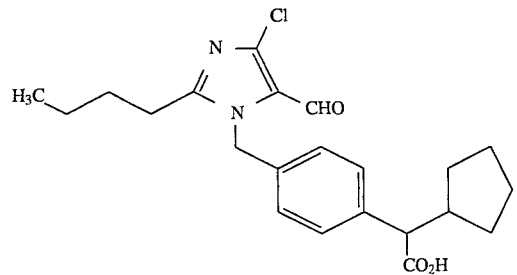

2.3 g (5 mmol) of the compound from Example IV are stirred at 25° C. for 5 h in 5 ml of dichloromethane and 5 ml of trifluoroacetic acid. After concentration, the crude product is chromatographed on silica gel 60 using dichloromethane/methanol (100:5). Yield: 1.8 g (87.6% of theory) Melting point: 95°–98° C.

Example VI

Methyl 2-{2-[4-(2-butyl-4-chloro-5-formyl-imidazol-1-yl-methyl)phenyl]-2-cyclopentyl}-acetamido-2-(2-hydroxyphenyl)acetate

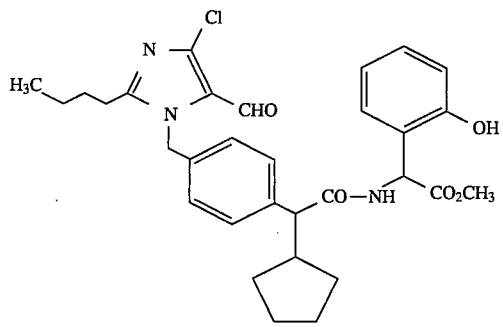

6.0 g (15 mmol) of the compound from Example V are dissolved in 180 ml of anhydrous tetrahydrofuran and reacted at 0° C. with 4.2 ml (30 mmol) of triethylamine and 1.26 ml (16.5 mmol) of methanesulphonyl chloride. After 1 hour, a solution of 3.92 g (18 mmol) of 2-hydroxyphenylglycine methyl ester hydrochloride, 1.82 g (15 mmol) of 4-(N,N-dimethylamino)pyridine and 2.52 ml (18 mmol) of triethylamine in 60 ml of tetrahydrofuran is added and the mixture is additionally stirred for 18 hours, the reaction temperature rising to room temperature. The crude mixture is added to water, adjusted to pH=2 to 3 using 2M hydrochloric acid and extracted with ether. The organic phase is dried with magnesium sulphate and evaporated. After chromatographic work-up on silica gel 60 (Merck, petroleum ether: ethyl acetate=2:1), 4.03 g (7.1 mmol) of the title compound are obtained. $R_f$=0.18 (dichloromethane:methanol=50:1)

PREPARATION EXAMPLES

Example 1

2-{2-[4-(2-Butyl-4-chloro-5-formyl-imidazol-1-yl-methyl)phenyl]-2-cyclopentyl}acetamido-2-phenyl-acetamide

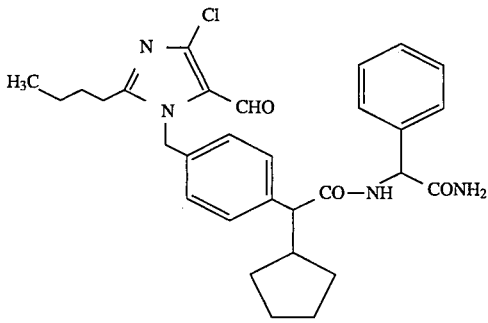

1.54 g (3.8 mmol) of the compound from Example V are reacted in anhydrous N,N-dimethylformamide at −30° C. with 1.06 ml (7.6 mmol) of triethylamine and 0.48 g (4.2 mmol) of methanesulphonyl chloride. After 1 hour, 0.69 g (4.6 mmol) of phenylglycinamide and 0.47 g (3.8 mmol) of 4-(N,N-dimethylamino)pyridine are added and the mixture is additionally stirred for 24 hours while slowly warming to room temperature. It is then poured into ether, treated with water and adjusted to pH=2 using 1M hydrochloric acid. The aqueous phase is reextracted with ether and the combined organic phases are washed several times with 0.01M hydrochloric acid. They are then extracted several times with aqueous sodium hydroxide solution of pH=10 and washed with water, the organic phase is dried with sodium sulphate and the solvent is evaporated. The crude product is purified by chromatography (silica gel 60, Merck 40–63 μm, petroleum ether: ethyl acetate=1:1). Yield: 1.56 g (2.9 mmol) of product. $R_f$=0.16 and 0.12 (petroleum ether:ethyl acetate=1:1)

The compounds shown in Table 1 are prepared in analogy to the procedure of Example 1:

TABLE 1

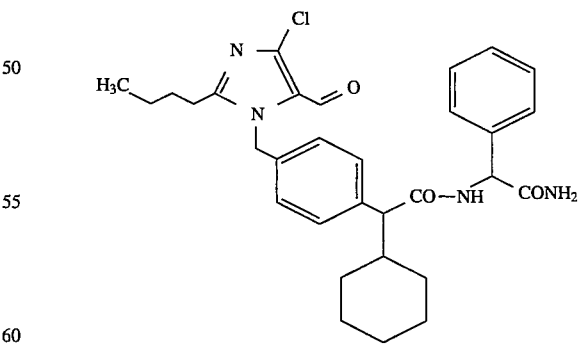

| Ex. No. | Diastereomer | $R^1$ | $R_f$ (solvent) |
|---------|--------------|-------|-----------------|
| 2 | 4 dia | cycloheptyl | 0.47 (A) |
| 3 | 4 dia | cyclohexylmethyl | 0.57 (B) |

Example 4

2-[4-(2-Butyl-4-chloro-5-formyl-imidazol-1-yl-methyl)phenyl]-2-cyclohexyl-N-phenylglycinamidoacetamide 0.42 g (1 mmol) of 2-[4-(2-butyl-4-chloro-5-formyl-imidazol-1-yl-methyl)phenyl]-2-cyclohexylacetic acid is treated at room temperature in 25 ml of dichloromethane with 0.2 g (2 mmol) of triethylamine and 0.23 g (1.5 mmol) of 1-hydroxy-1H-benzotriazole in 5 ml of tetrahydrofuran and the mixture is cooled to 0° C. After addition of 0.31 g (1.5 mmol) of dicyclohexylcarbodiimide in 10 ml of dichloromethane and stirring for 30 minutes, a solution of 0.32 g (1.2 mmol) of phenylglycinamide and 0.1 g (1.2 mmol) of triethylamine in 10 ml of dichloromethane is added and the mixture is stirred overnight at room temperature. For work-up, the mixture is extracted after addition of dichloromethane, and the combined organic phases are dried over sodium sulphate, filtered, concentrated and chromatographed on silica gel 60 (ethyl acetate/petroleum ether=1:1). Yield: 0.31 g (0.56 mmol) 56% of theory $R_f$=0.52 (dichloromethane/methanol=9:1)

Example 5

2-[4-(2-Butyl-4-chloro-5-hydroxymethyl-imidazol-1-ylmethyl)phenyl]-2-cyclohexyl-N-phenylglycinamidoacetamide

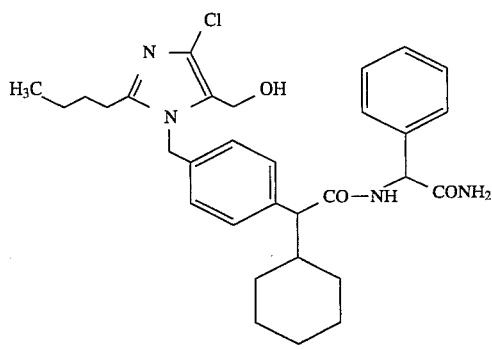

0.15 g (0.3 mmol) of 2-[4-(2-butyl-4-chloro-5-formylimidazol-1-yl-methyl)phenyl]-2-cyclohexyl-N-phenylglycinamidoacetamide are treated at room temperature in 5 ml of ethanol with 10 mg of sodium borohydride and the mixture is stirred at room temperature for 2 hours. For work-up, water is added and the mixture is adjusted to pH 4–5 using 1N acetic acid and extracted three times with ethyl acetate. The combined organic phases are dried over sodium sulphate, filtered and concentrated. Yield: 0.16 g (0.29 mmol) 98% of theory $R_f$=0.48 (dichloromethane/methanol=9:1)

Example 6

2-{2-[4-(2-Butyl-4-chloro-5-hydroxymethyl-imidazol-1-yl-methyl)phenyl]-2-cyclopentyl}acetamido2-phenyl-acetamide

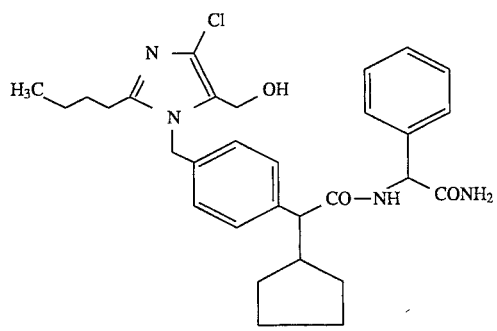

1.37 g (2.6 mmol) of the compound from Example 1 are reacted at 20° C. in 15 ml of ethanol with 0.10 g (2.6 mmol) of sodium borohydride. If reaction is incomplete (TLC checking), further sodium borohydride is added. after 2 hours; After a total of 3 hours, water and ether are added, excess borohydride is destroyed using hydrochloric acid at pH=2, and the mixture is then adjusted to pH=7.5 using 1M aqueous sodium hydroxide solution and extracted several times with ether. The organic phase is dried using sodium sulphate and evaporated. Yield: 1.06 g (2.0 mmol) $R_f$=0.78 and 0.75 (dichloromethane:methanol=5:1)

The compounds shown in Table 2 are prepared in analogy to the procedure of Example 6:

TABLE 2

| Ex. No. | Diastereoisomer | $R^1$ | $R^2$ | $R^3$ | $R_4$ | $R^5$ | $R_f$(solvent) |
|---|---|---|---|---|---|---|---|
| 7 | rac dia A | cycloheptyl | H | H | H | H | 0.37(A) |
| 8 | rac dia B | cycloheptyl | H | H | H | H | 0.26(A) |

TABLE 2-continued

[Structure: imidazole with Cl, CH2OH, butyl, and N-CH2-phenyl-CHR1-CON(R2)-CHR(Ar-R3)-CON(R4)(R5)]

| Ex. No. | Diastereoisomer | R¹ | R² | R³ | R₄ | R⁵ | R_f(solvent) |
|---------|-----------------|-----|-----|------|-----|-----|--------------|
| 9 | 4 dia | cyclopentyl | H | 2-OH | H | H | 0.42 (C) |
| 10 | 4 dia | cyclohexylethyl | H | H | H | H | 0.23/0.18 (A) |

Example 11

2-{2-[4-(2-Butyl-4-chloro-5-formyl-imidazol-1-yl-methyl)phenyl]-2-cyclopentyl}-acetamido-2-(2-hydroxyphenyl)acetamide

[Structure]

60 mg (0.11 mmol) of the compound from Example VI are dissolved in 2 ml of anhydrous tetrahydrofuran and reacted with 1 ml of 25% strength aqueous ammonia solution (6 hours at 50° C.). The mixture is then adjusted to pH=7 using 0.1M sulphuric acid and extracted several times with ether. The organic phase is dried using magnesium sulphate and evaporated. After removal of the residual solvent in a high vacuum, 40 mg (0.07 mmol) of product are obtained. $R_f$=0.21 (petroleum ether:acetic acid=1:1)

The compounds shown in Tables 3 and 4 are the separated diastereomers of Examples 1 and 2 and can be prepared by separation of these according to customary methods:

TABLE 3

[Structure with CHO group]

| Ex. No. | Diastereoisomer | R_f(solvent) |
|---------|-----------------|--------------|
| 12 | dia A | 0.16 (D) |
| 13 | dia B | 0.12 (D) |
| 14 | dia C | 0.16 (D) |
| 15 | dia D | 0.12 (D) |

TABLE 4

[Structure with CH2OH group]

| Ex. No. | Diastereoisomer | R_f(solvent) |
|---------|-----------------|--------------|
| 16 | dia A | 0.78 (E) |
| 17 | dia B | 0.75 (E) |

TABLE 4-continued

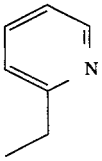

| Ex. No. | Diasteroisomer | R_f(solvent) |
|---|---|---|
| 18 | dia C | 0.78 (E) |
| 19 | dia D | 0.75 (E) |

The compounds shown in Table 5 are prepared in analogy to the procedure of Example 11:

TABLE 5

| Ex. No. | $R^5$ | R_f(solvent) |
|---|---|---|
| 20 | $CH_2CO_2CH_2CH_3$ | 0.35 (F) |
| 21 | $CH_2CH_2N(CH_3)_2$ | 0.47 (E) |
| 22 | (2-ethylpyridyl) | 0.53 (G) |
| 23 | (2-methylpyridyl) | 0.75 (E) |
| 24 | (methylcyclohexyl) | 0.61 (G) |
| 25 | $CH_2CH_2OH$ | 0.33 (G) |
| 26 | (methylphenyl) | 0.37 (H) |
| 27 | $CH_3$ | 0.14 (I) |

The compounds shown in Table 6 are prepared in analogy to the procedure of Example 6:

TABLE 6

| Ex. No. | L | Z | R_f(solvent) |
|---|---|---|---|
| 28 | $CH_3$ | $NH_2$ | 0.32 (I) |

The compounds shown in Table 7 are prepared in analogy to the procedure of Example 1:

TABLE 7

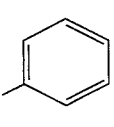

| Ex. No. | L | Z | R_f(solvent) |
|---|---|---|---|
| 29 | $CH_3$ | $NH_2$ | 0.06 (D) |

Example 30

<2-{2-[4-(2-Butyl-4-chloro-5-hydroxymethyl-imidazol-1-ylmethyl)phenyl-2-cyclopentyl}acetamido-2-phenyl-acetamido>-acetic acid

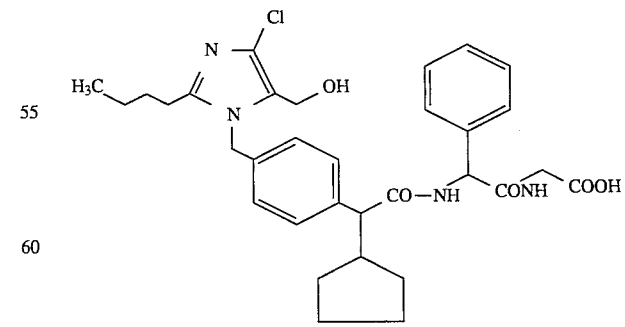

60 mg (0.1 mmol) of the compound from Example 20 are dissolved in 2 ml of ethanol and reacted for 1 hour at 22° C. with 4 ml of aqueous 1M sodium hydroxide solution. The reaction mixture is diluted with water, the ethanol component is evaporated and the product is precipitated by acidifying with 2M hydrochloric acid. The precipitate is washed with water and dried in a high vacuum over Sicapent (Merck): 43 mg. $R_f$=0.60 (dichloromethane:methanol=10:1)

We claim:

1. A phenylglycinamide of the formula

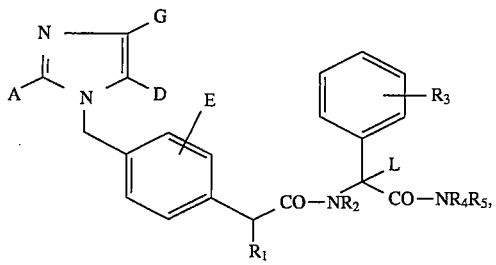

in which

A represents straight-chain or branched alkyl or alkenyl each having up to 8 carbon atoms, or represents cycloalkyl having 3 to 8 carbon atoms, G represents hydrogen, halogen or perfluoroalkyl having up to 5 carbon atoms, D represents a group of the formula —$CH_2$—$OR^6$ or —CO—$R^7$, in which $R^6$ denotes hydrogen or straight-chain or branched alkyl having up to 8 carbon atoms, $R^7$ denotes hydrogen, hydroxyl or straight-chain or branched alkoxy having up to 8 carbon atoms, E represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl, L represents hydrogen or straight-chain or branched alkyl having up to 4 carbon atoms, $R^1$ represents cycloalkyl having 3 to 8 carbon atoms, or represents straight-chain or branched alkyl having up to 8 carbon atoms, which is optionally substituted by cycloalkyl having 3 to 8 carbon atoms, $R^2$ represents hydrogen or straight-chain or branched alkyl having up to 6 carbon atoms, $R^3$ represents hydrogen, hydroxyl, halogen or straight-chain or branched alkoxy having up to 6 carbon atoms, $R^4$ and $R^5$ are identical or different and represent hydrogen, pyridyl, cycloalkyl having 3 to 8 carbon atoms, phenyl, or straight-chain or branched alkyl having up to 8 carbon atoms, which is optionally substituted by hydroxyl, pyridyl, carboxyl, straight-chain or branched alkoxycarbonyl having up to 6 carbon atoms or by a group of the formula —$NR^8R^9$, in which $R^8$ and $R^9$ are identical or different and denote hydrogen or straight-chain or branched alkyl having up to 4 carbon atoms or $R^4$ and $R^5$, together with the nitrogen atom, form a morpholine piperazine or piperidine ring or a salt therof.

2. A phenylglycinamide or salt thereof according to claim 1, in which

A represents straight-chain or branched alkyl or alkenyl each having up to 6 carbon atoms, or represents cyclopropyl, cyclobutyl, cyclopentyl, cyclohexyl or cycloheptyl, G represents hydrogen, fluorine, chlorine, bromine or perfluoroalkyl having up to 4 carbon atoms, D represents a group of the formula —$CH_2$—$OR^6$ or —CO—$R^7$, in which $R^6$ denotes hydrogen or straight-chain or branched alkyl having up to 6 carbon atoms, $R^7$ denotes hydrogen, hydroxyl or straight-chain or branched alkoxy having up to 6 carbon atoms, E represents hydrogen, fluorine, chlorine, bromine, trifluoromethyl, carboxyl or straight-chain or branched alkyl, alkoxy or alkoxycarbonyl each having up to 4 carbon atoms, L represents hydrogen or methyl $R^1$ represents cyclopropyl, cyclopentyl, cyclohexyl or cycloheptyl, or represents straight-chain or branched alkyl having up to 4 carbon atoms, which is optionally substituted by cyclopropyl, cyclopentyl, cyclohexyl or cycloheptyl, $R^2$ represents hydrogen or straight-chain or branched alkyl having up to 4 carbon atoms, $R^3$ represents hydrogen, hydroxyl, fluorine, chlorine, bromine or straight-chain or branched alkoxy having up to 4 carbon atoms, $R^4$ and $R^5$ are identical or different and represent hydrogen, pyridyl, cyclopentyl, cyclohexyl, phenyl or straight-chain or branched alkyl having up to 6 carbon atoms, which is optionally substituted by hydroxyl, pyridyl, carboxyl, straight-chain or branched alkoxycarbonyl having up to 4 carbon atoms or by a group of the formula —$NR^8R^9$, in which $R^8$ and $R^9$ are identical or different and denote hydrogen or methyl, or $R^4$ and $R^5$, together with the nitrogen atom, form a morpholine, piperazine or piperidine ring, and their salts.

3. A phenylglycinamide or salt thereof according to claim 1, in which

A represents straight-chain or branched alkyl or alkenyl each having up to 4 carbon atoms, or represents cyclopropyl, cyclopentyl or cyclohexyl, G represents hydrogen, fluorine, chlorine or perfluoroalkyl having up to 2 carbon atoms, D represents a group of the formula —$CH_2$—$OR^6$ or —CO—$R^7$, in which $R^6$ denotes hydrogen or straight-chain or branched alkyl having up to 4 carbon atoms, $R^7$ denotes hydrogen, hydroxyl or straight-chain or branched alkoxy having up to 4 carbon atoms, E represents hydrogen, fluorine, chlorine, bromine, trifluoromethyl, trifluoromethoxy or methyl L represents hydrogen or methyl, $R^1$ represents cyclopentyl, cyclohexyl or cycloheptyl, or represents straight-chain or branched alkyl having up to 3 carbon atoms, which is optionally substituted by cyclopentyl, cyclohexyl or cycloheptyl, $R^2$ represents hydrogen, methyl or ethyl, $R^3$ represents hydrogen, hydroxyl, fluorine, chlorine, bromine or methoxy, R⁴ and R⁵ are identical or different and represent hydrogen, pyridyl, cyclohexyl, phenyl or straight-chain or branched alkyl having up to 4 carbon atoms, which is optionally substituted by hydroxyl, pyridyl, carboxyl, straight-chain or branched alkoxycarbonyl having up to 3 carbon atoms, amino or dimethylamino, or R⁴ and R⁵, together with the nitrogen atom, form a morpholine, piperazine or piperidine ring, and their salts.

4. A phenylglycinamide according to claim 1 wherein such compound is 2-{2-[4-(2-Butyl-4-chloro-5-formyl-imidazol-1-yl-methyl)-phenyl]-2-cyclopentyl}acetamido-2-phenyl-acetamide of the formula

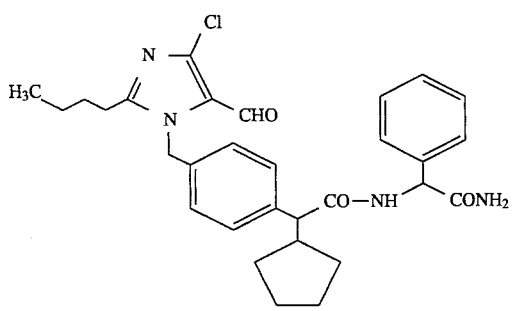

or a salt thereof.

5. A phenylglycinamide according to claim 1 wherein such compound is 2-{2-[4-(2-Butyl-4-chloro-5-formyl-imidazol-1-yl-methyl)-phenyl]-2-cycloheptyl}acetamido-2-phenyl-acetamide of the formula

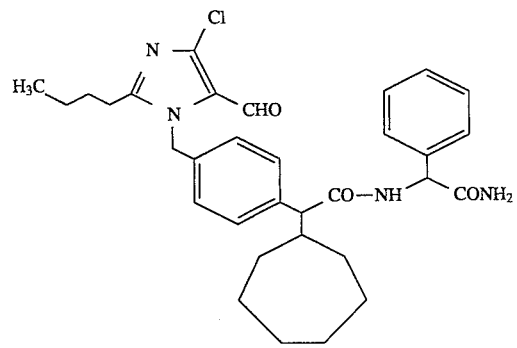

or a salt thereof.

6. A phenylglycinamide according to claim 1 wherein such compound is 2-[4-(2-Butyl-4-chloro-5-hydroxymethyl-imidazol-1-yl-methyl)phenyl]-2-cyclohexyl-N-phenylglycinamidoacetamide of the formula

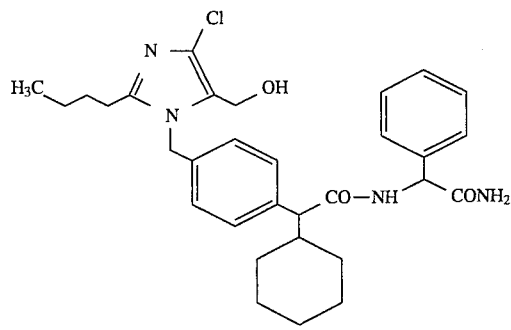

or a salt thereof.

7. A phenylglycinamide according to claim 1 wherein such compound is 2-{2-[4-(2-Butyl-4-chloro-5-hydroxymethyl-imidazol-1-yl-methyl)phenyl]-2-cyclopentyl}acetamido2-phenyl-acetamide of the formula

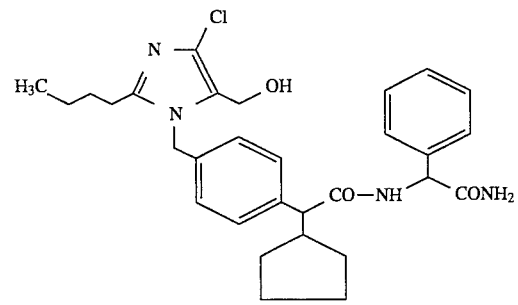

or a salt thereof.

8. A composition for the treatment of arterial hypertension and atherosclerosis comprising an amount effective therefore of a compound or salt thereof according to claim 1 and a pharmacologically acceptable diluent.

9. The method of treating arterial hypertension and atherosclerosis in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,576,342
DATED : November 19, 1996
INVENTOR(S) : Muller, et al.

It is certified that error appears in the above-indentified patent and that said Letters Patent is hereby corrected as shown below:

Title Page     item [75] Inventors: Last Inventor delete " ; Siegfried Zaiss, Wuppertal, all of Germany "

Title Page     item [73]: Insert -- [8] Notice: The term of this Patent shall not extent beyond the expiration date of Pat. Nos. 5,420,149 and Pat. No. 5,352,687. --

Title Page     After [45] Date of Patent: Insert -- * --

Col. 24, line 40    Delete " and their salts "

Col. 25, line 10    Delete " and their salts "

Signed and Sealed this

Fifteenth Day of June, 1999

Attest:

Attesting Officer

Q. TODD DICKINSON

Acting Commissioner of Patents and Trademarks